US009597448B2

(12) United States Patent
Barvais et al.

(10) Patent No.: US 9,597,448 B2
(45) Date of Patent: Mar. 21, 2017

(54) COMPUTER-CONTROLLED INTRAVENOUS DRUG DELIVERY SYSTEM

(75) Inventors: Luc Barvais, Wemmel (BE); Eddy Coussaert, Waterloo (BE)

(73) Assignee: Université Libre de Bruxelles, Brussels (BE)

( * ) Notice: Subject to any disclaimer, the term of this patent is extended or adjusted under 35 U.S.C. 154(b) by 2217 days.

(21) Appl. No.: 10/584,182

(22) PCT Filed: Dec. 21, 2004

(86) PCT No.: PCT/BE2004/000180
§ 371 (c)(1),
(2), (4) Date: Aug. 3, 2007

(87) PCT Pub. No.: WO2005/061028
PCT Pub. Date: Jul. 7, 2005

(65) Prior Publication Data
US 2007/0282251 A1   Dec. 6, 2007

(30) Foreign Application Priority Data

Dec. 24, 2003 (EP) .................................... 03447308

(51) Int. Cl.
*A61M 5/142* (2006.01)
*A61M 5/172* (2006.01)
*G06F 19/00* (2011.01)

(52) U.S. Cl.
CPC ......... *A61M 5/142* (2013.01); *G06F 19/3468* (2013.01); *A61M 5/1723* (2013.01);
(Continued)

(58) Field of Classification Search
CPC ............ A61M 5/142; A61M 2202/048; A61M 5/1723; A61M 2205/18; A61M 2205/33;
(Continued)

(56) References Cited

U.S. PATENT DOCUMENTS 5,041,086 A   8/1991   Koenig et al.
5,713,856 A   2/1998   Eggers et al.
(Continued)

FOREIGN PATENT DOCUMENTS

WO   99/10029   3/1999

OTHER PUBLICATIONS

Alvis et al., "Computer-assisted Continuous Infusions of Fentanyl during Cardiac Anesthesia: Comparison with a Manual Method." *Anesthesiology* 63(1985): 41-49.
(Continued)

*Primary Examiner* — Manuel Mendez
(74) *Attorney, Agent, or Firm* — Merchant & Gould P.C.

(57) ABSTRACT

The present invention relates to a system for computer-aided intravenous delivery of anesthetics and/or other drugs to a patient, wherein said system comprises an Infusion Controller that delivers an amount of drug(s) to a patient; possibly a DataLogger Controller with one or more Sensors adapted so as to be coupled to a patient and to generate signals reflecting one or more health conditions or statuses of the patient; a Communication Controller connected with the infusion pumps and/or monitors; a Session Controller that carries out the modeling of anesthesia procedures and is arranged to run a first procedure and to dynamically adapt said first procedure and/or select and run a second procedure based upon one or more of said sensors' output and/or observation from a physician; a Graphic User Interface to display different views of the system and to accept user input; a set of interfaces used to link the Infusion, Datalogger and Session Controllers to views displayed by the Graphical User Interface; a Processor or Infusion Session Manager that integrates the Graphic User Interface, the Infusion Controller, the DataLogger Controller, the Communication Controller and the Session Controller and that
(Continued)

steers drug delivery, wherein the system contains a set of configurable written procedures to steer intravenous anesthetic drag delivery and/or other drug delivery, whereby said procedures have been adapted to the type of surgical action and/or therapy, adapted to the patient's physical condition, and adapted to the type of drugs, tools and theoretical models used.

The system of the present invention finds its use among others in intravenous anesthesia (IVA) and in cancer therapy.

19 Claims, 5 Drawing Sheets

(52) U.S. Cl.
CPC .............. *A61M 2005/14208* (2013.01); *A61M 2202/048* (2013.01); *A61M 2205/18* (2013.01); *A61M 2205/33* (2013.01); *G06F 19/3437* (2013.01)

(58) Field of Classification Search
CPC ...... A61M 2005/14208; G06F 19/3468; G06F 19/3437
USPC ... 604/65–67, 131, 151, 246, 503, 504, 512, 604/890.1
See application file for complete search history.

(56) References Cited

U.S. PATENT DOCUMENTS

| | | | | |
|---|---|---|---|---|
| 5,733,259 | A * | 3/1998 | Valcke | A61M 5/1723 128/DIG. 12 |
| 6,126,642 | A * | 10/2000 | Kriesel | A61M 5/1424 604/131 |
| 7,559,926 | B1 * | 7/2009 | Blischak | A61M 5/14276 604/890.1 |
| 2002/0077852 | A1 * | 6/2002 | Ford et al. | 705/2 |
| 2002/0169636 | A1 * | 11/2002 | Eggers | A61B 5/417 705/3 |
| 2003/0045858 | A1 | 3/2003 | Struys et al. | |
| 2003/0051737 | A1 * | 3/2003 | Hickle | A61M 5/1723 128/898 |
| 2003/0140929 | A1 * | 7/2003 | Wilkes | G06Q 50/24 128/898 |
| 2003/0217747 | A1 | 11/2003 | Hickle et al. | |

OTHER PUBLICATIONS

Gall et al., "Benefcial effects of endotracheal extubation on ventricular performance." *J. Thorac Cardiovascular Surgery* 95(1988): 819-827.

Schreiber, P.J., "Measures for reducing the risks of anesthesia," *Anaesthesiol Reanim.* (1990) 15 (5): 287-97 English Abstract Only.

Absalom et al., "Closed-loop control of propofol anesthesia using bispectral index™: performance assessment in patients receiving computer-controlled propofol and manually controlled remifentanil infusions for minor surgery," *British Journal of Anesthesia* (2003) 90 (6): 737-41.

Chastre et al., "Ventilator-associated pneumonia," *Am. J. Respir. Crit. Care Med.* (2002) 165: 867-903.

Cheng et al., "Fast-track cardiac surgery: Economic implications in postoperative care," *J. Card. and Vascular Anesthesia* (1998) 12 (1): 72-79.

Drummond et al., "Monitoring depth of anesthesia," *Anesthesiology* (2000) 93 (3): 876-882.

He et al., "Pulmonary disposition of propofol in surgical patients," *Anesthesiology* (2000) 93: 986-91.

Marsh et al., "Pharmacokinetic model driven infusion of propofol in children," *British Journal of Anesthesia* (1991) 67: 41-48.

Minto et al., "Influence of age and gender on the pharmacokinetics and pharmacodynamics of remifentanil," *Anesthesiology* (1997) 86: 10-13.

Schnider et al., "The influence of propofol pharmacodynamics," *Anesthesiology* (1999) 90 (6): 1502-1516.

Struys et al., "Comparision of closed-loop controlled administration of propofol using bispectral index as the controlled variable versus "Standard Practice" controlled administration," *Anesthesiology* (2001) 95: 6-17.

Westerlind et al., "The use of continuous positive airway pressure by face mask and thoracic epidural analgesia after lung transplantation," *J. Card. and Vascular Anesthesia* (1999) 13 (3): 249-252.

Shafer, Steven L. "The Pharmacokinetic and Pharmacodynamic Basis of Target Controlled Infusion", Chapter—Standford University (2014).

TIVA Total Intravenous Anesthesia: "Target Controlled Infusion—TCI ; part 1", Austrian Anesthesia, Feb. 25, 2005, 2 pages. Previously accessible Online at: http://www.anesthesia.at/anesthesiology/tiva.html.

* cited by examiner

DataLogger Controller

Communication Controller

COMPUTER-CONTROLLED INTRAVENOUS DRUG DELIVERY SYSTEM

FIELD OF THE INVENTION

The present invention relates to apparatuses and methods for controlling and steering intravenous anesthesia (IVA) and/or the application of other intravenous drugs to a patient in a safe and user friendly way. Via the systems of the invention less experienced anesthetists profit from expert knowledge stored, retrievable and usable via the system.

BACKGROUND OF THE INVENTION

Anesthesia can be considered as an amalgam of several components of which the principal components are hypnotics, amnesics, analgesics, including control of motor activity and of the reactions of the autonomous nervous system.

The aim of present-day anesthesia is to assure:
an induction of anesthesia that is easy and fast
stable haemodynamics and a dynamic balance between analgesia, hypnosis and amnesia during the course of the surgery
muscular relaxation with the aid of curare
a rapid and comfortable recovery from narcosis.

Intravenous anesthesia (IVA) implies the intravenous injection of several drugs following a pharmacokinetic model. Anesthetic drugs include hypnotics to control hypnosis of the patient, morphinomimetics to control analgesia and curare for muscle relaxation. Traditionally these drugs were applied manually by the anesthetist via syringes. The traditional titration process is time-consuming, labor-intensive and vulnerable to human errors. In addition to that, there is a factor of unpredictability involved which is caused among others by patient variability and which can not fully be taken into account by pharmacodynamic and/or pharmacokinetic models.

The anesthetist is multi-tasked both physically and cognitively during the course of a surgical operation. It is known that human errors are ready to incur upon repetitive tasks such as the constant monitoring of electronic and other signals, the repetitive delivery of drugs via injections etc. Another factor to consider is the fact that serious complications can occur at any time during an operation, which can evolve in a bad direction very rapidly.

It is thus imperative to alleviate the anesthetist's tasks as much as possible, without departing too much from the principle that the "physician knows best". Better control of IVA and a more comfortable recovery therefrom will also benefit the patient.

The benefit for the anesthetist will be that he can focus his attention on surveillance of the patient and on important events in the surgery such as for instance cardio-respiratory reanimation during a single or double lung transplantation. It is known that the risk of human errors decreases in view of a reliable supportive tool. The human brain is very performing regarding the taking of decisions in complex situations; but when a human being has to survey continuously a monotonous parameter the performance of the human brain falls with an increased hazard for accidents (Schreiber, 1990, Reanim 15: 287-97).

The patient not only benefits from the reduction of risks, there are other advantages linked to better controlled IVA. It has for instance been demonstrated that a fast recovery from a surgical lung transplantation without complications and a fast decoupling from mechanical ventilation apparatuses benefits the patient (Westerlind, JCTVA, 1999, Tran SFAR 2003). A non-justified mechanical ventilation can even be responsible for bacterial colonization of the upper airways, which favors possibly detrimental nosocomial pneumopathies (Chastre and Fagon, Am J Respir Crit Care Med 2002). It has further been shown that a precocious tracheal extubation after a non-complicated cardiac surgery would improve the patient's ventricular performance (Gall et al; 188, J Thorac Cardiovasc Surg 95: 819-27), his cognitive functions and diminishes the occurrence of intrapulmonary shunts (Cheng, 1998, J Cardiothorac Vasc Anesth 12: 35-40). It has also been shown that by subjecting an anesthetic to a monitoring of the depth of anesthesia one is able to obtain an anesthesia more stable with less episodes of hypotension and a faster recovery (Struys anesthesia 2001).

The field of intravenous anesthesia (IVA) has undergone an important progress the last years due to the fact that intravenous (IV) agents with a fast-working and short-lived activity have been put on the market. Certainly the introduction of propofol in the late eighties made this "boost" possible, because in contrast to other hypnotics, like barbiturates and etomidate, propofol is really the best suited intravenous agent for maintenance of anesthesia.

However, in contrast to the rapid progress seen in the field of inhalational anesthetics, introduction of new intravenous drugs has not resulted in the rapid development of new and widely accepted sophisticated intravenous delivery systems. Today, intravenous agents are still commonly administered by manual bolus on a dose/kg basis.

Several new drug delivery systems for intravenous anesthesia have been developed, and introduced during the last 10 years. These are pumps with faster infusion rates and special features, such as "hands-free" bolus delivery function. Despite these sophisticated manually controlled infusion pumps, (T)IVA is sometimes perceived as being more complicated to perform and difficult to control than inhalational anesthesia.

Target-controlled infusion (TCI) apparatuses introduced onto the market comprise an infusion pump attached to a computer (microprocessor). The computer's program contains a pharmacokinetic model, describing the elimination and metabolism of the drug within the body, and pharmacokinetic data for widely different patient populations. The target drug concentration and data specific to the patient undergoing surgery, such as age and body weight, are entered into the system by the anesthetist. From its pharmacokinetic model, the TCI system determines the initial loading dose required to achieve the target concentration and the infusion rate to sustain it, and controls the infusion automatically (http://www.anesthesia.at/anesthesiology/tiva.html).

Entirely computer-controlled delivery systems have been introduced, but were not readily accepted by clinicians. It is however known that the perfusion of hypnotics with the aid of a closed-loop control allows reduction of the total amount of anesthetics being given, allows a faster recovery afterwards and facilitates decoupling from mechanical ventilation machines (Struys 2002). It has further been shown that at least cardiac surgery benefits from TCI (Target Controlled Infusion or computer-aided IVA and choice of anesthetic concentrations) compared to a manual technique (Alvis et al, 1985, Anesthesiology 63: 41-9)

US patent application 2003/0051737 discloses apparatuses and methods for providing computer-assisted titration of the level of sedative, amnesic and/or analgesic drugs in a controlled and a transparent fashion that allows time for manual and/or automatic assessment of the patient's response to changing drug levels. The disclosure of this document is herein incorporated in its entirety by reference thereto, especially with respect to the background of the invention.

Closed-loop control of the bi-spectral analysis of the electroencephalogram, the BIS index, has been the subject of several publications (see e.g. Absalom and Kenny, 2003, Br J Anaesth 90: 737-41).

US application US2002/0169636 discloses a system and method for providing care to a patient, comprising a patient care device having a number of configuration databases stored in a memory in the device. Transferring patient-specific info to the patient care device enables the selection of a specific configuration database from the plurality of configuration databases, the selection being based at least partially upon the patient-specific information. The system is static in the sense that the selected protocol only executes a number of predetermined instructions.

Patent application WO99/10029 relates to an automated medication infusion device. It receives prescription information including information pertaining to a medication prescribed for a patient. The system is only capable of performing predefined tasks. It does not contain any intelligence to propose any other action than merely alerting a clinician when the prescribed medication is found inappropriate to administer to the patient.

AIMS OF THE INVENTION

It is an aim of the present invention to provide computer-assisted systems and methods that allow transfer of the knowledge of an expert, preferably an anesthetist expert, to other anesthetists and/or to other (trained) medical personnel such as nurses or medical assistants.

The improved IVA systems and methods of the invention are flexible, easy to use and transparent.

It is a further aim of the present invention to make IVA safer to use therewith.

It is an aim of the invention to provide such safe systems and methods for use during a surgical operation.

The improved intravenous anesthesia protocols and steering systems of the invention allow optimal anesthesia and recovery therefrom.

The systems and methods of the invention are equally well applicable in cancer therapy wherein intravenous drugs are used.

DESCRIPTION OF THE FIGURES

The FIG. 1 represents a flow chart showing interactions between different components of the system.

The FIG. 2 represents the available interfaces of the Session Controller and their usage.

Figure 3:
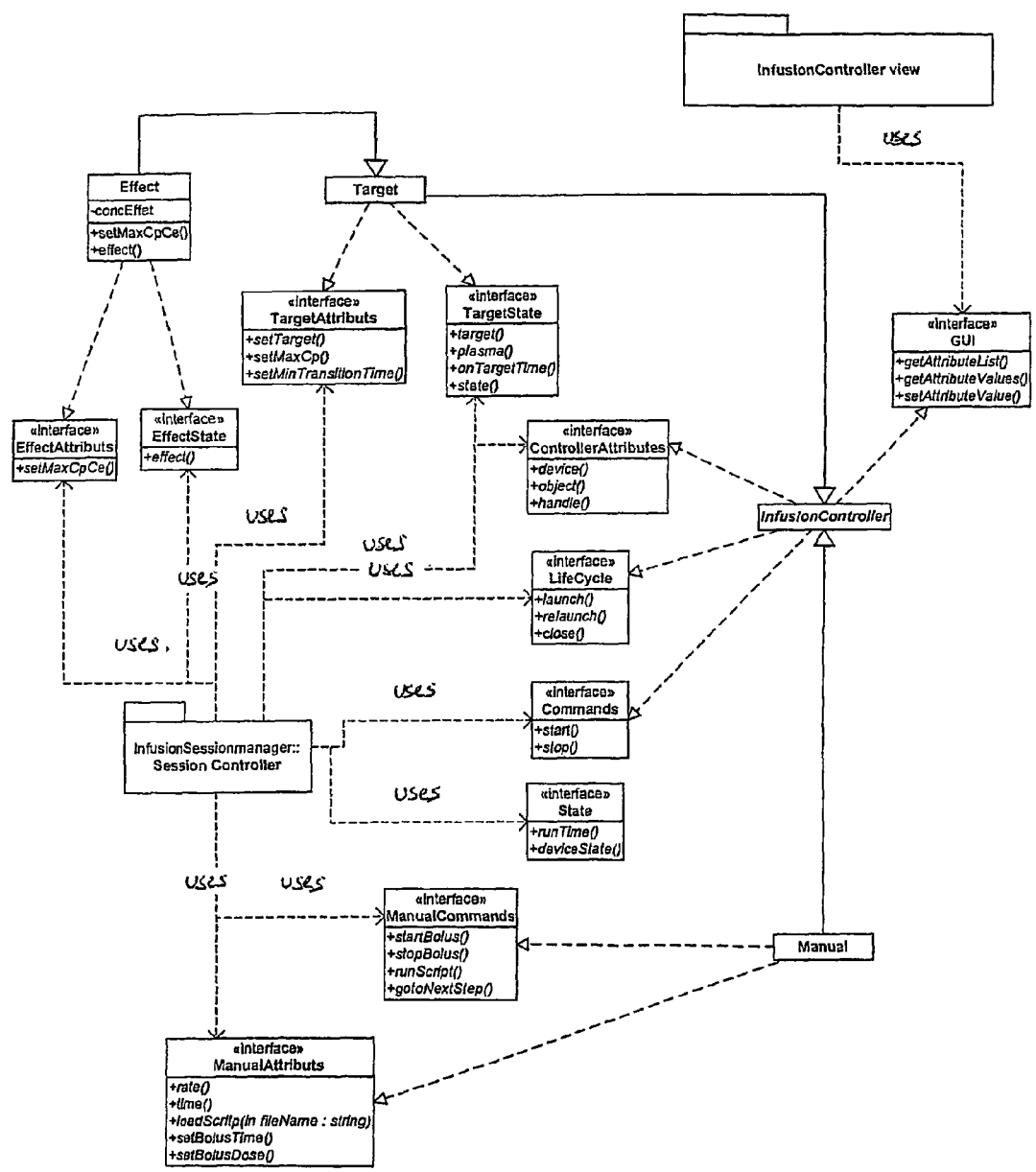

The FIG. 3 represents the available interfaces of the Infusion Controller and their usage.

Figure 4:
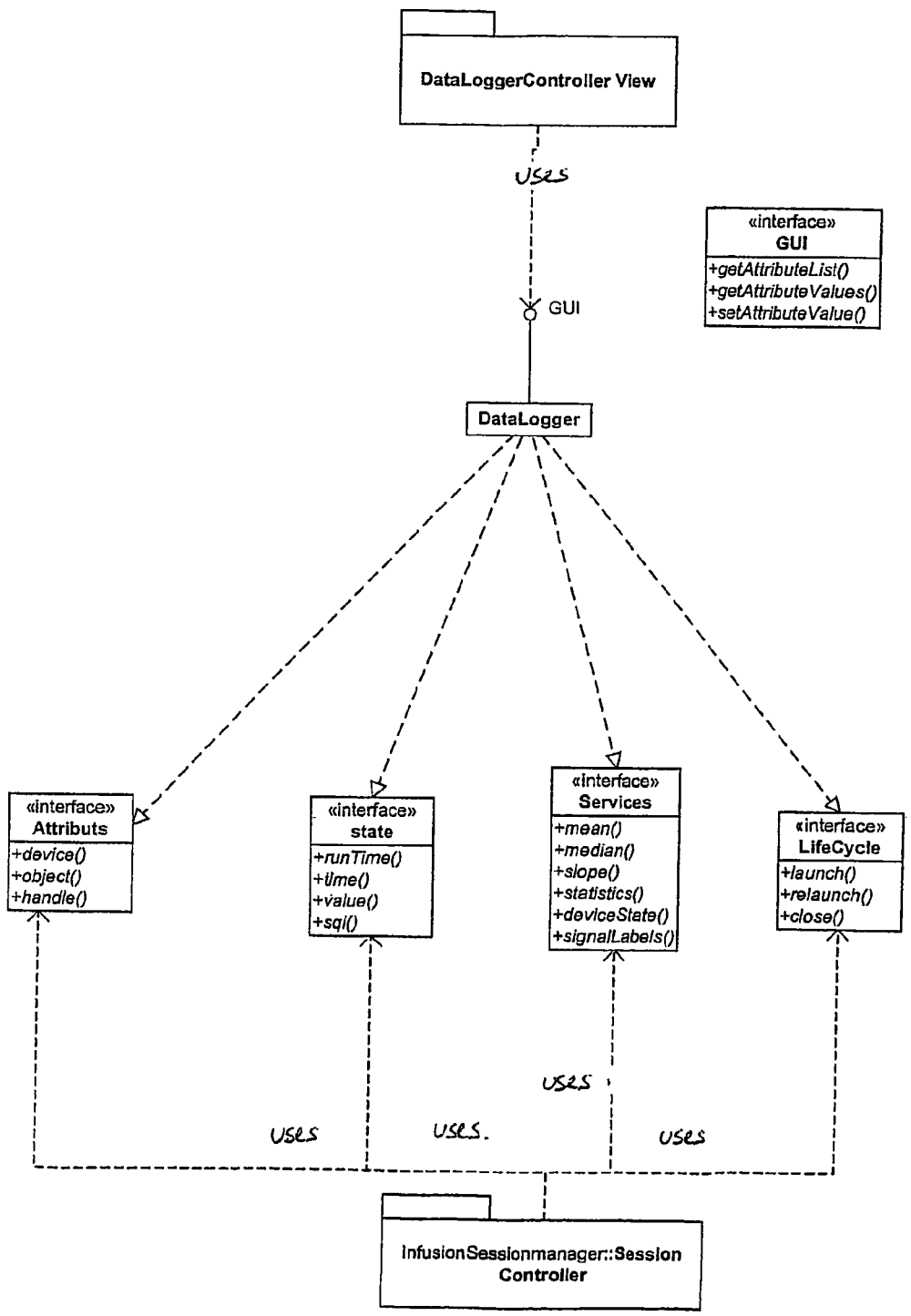

The FIG. 4 represents the available interfaces of the DataLogger Controller and their usage.

Figure 5:
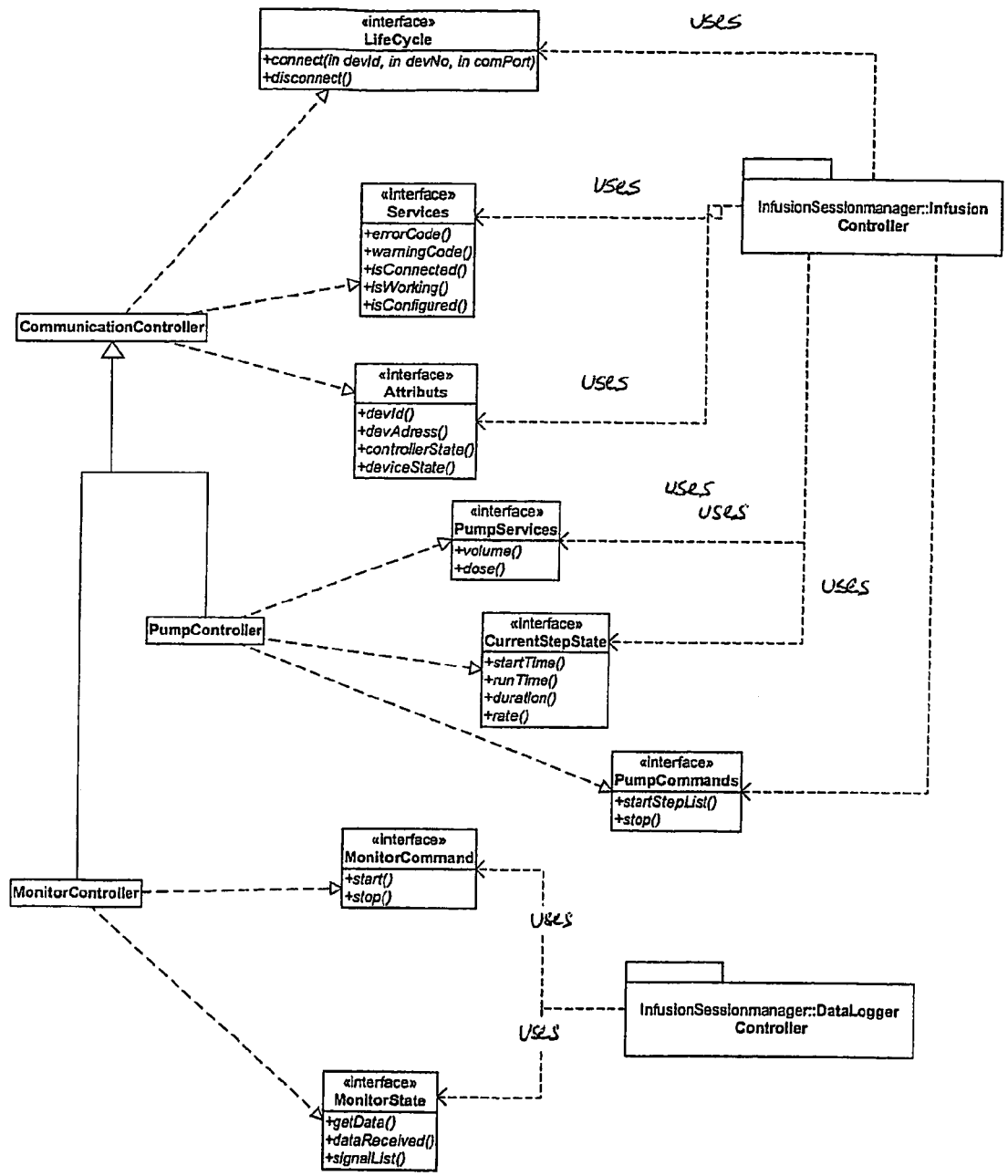

The FIG. 5 represents the available interfaces of the Communication Controller and their usage.

DESCRIPTION OF THE INVENTION

The System and its Components

A first aspect of the invention relates to a system for computer-aided intravenous delivery of anesthetics and/or other drugs to a patient. The system comprises:

- an Infusion Controller that delivers an amount of drug(s) to a patient;
- possibly a DataLogger Controller with one or more Sensors adapted so as to be coupled to a patient and to generate signals reflecting one or more health conditions or statuses of the patient;
- a Communication Controller connected with the infusion pumps and/or monitors;
- a Session Controller that carry out the modeling of the anesthesia procedures established or proposed by an expert (in term of procedures, tools, constraints, interaction and event tables). Said controller should at least check that all constraints are respected, supervise execution of the procedures launched either internally by interaction rules or externally by selecting an event in a table. The session controller is arranged to run a first procedure and to dynamically adapt said first procedure and/or to select and run a second procedure based upon one or more of said sensors' output and/or observation from a physician;
- a Graphic User Interface to display different views of the system and to accept user input;
- a set of interfaces used to link the Infusion, Datalogger (if present) and Session Controllers to views displayed by the Graphical User Interface;
- a Processor or Infusion Session Manager that integrates the User Interface, the Infusion Controller, the DataLogger Controller (if present), the Communication Controller and the Session Controller and that steers drug delivery.

The system according to the invention differs from the prior art in that it introduces a modeling of (anesthetic) procedures in a way that reliable expert knowledge is passed onto the anesthetist in charge of the operation and/or his assistant of that day.

The system of the invention hereto contains a set of configurable written procedures to steer intravenous anesthetic drug delivery and/or other drug delivery, whereby said procedures have been adapted to the type of surgical action and/or therapy, adapted to the patient's physical condition, and adapted to the type of drugs, tools and theoretical models used. The set of procedures (which reflect the knowledge and expertise of a very experienced anesthetist) is put at the disposition of the user (clinician, anesthetist, nurse or assistant in charge) who is not obliged to follow these procedures blindly. Reversion to a manual mode is possible at any time.

The level of experience of the person in charge or the user, determines whether he or she will be allowed to configure, model or adapt any of the written procedures and/or may only be allowed to make use of existing procedures without the possibility of changing anything to the system. According to an embodiment of the present invention, three levels of competence or experience are set: that of an expert (user of level 3), that of a qualified user (user of level 2) and that of any user (user of level 1).

Changes in the procedure may be launched or triggered by the internal state of the system (i.e. the internal state of the system determines future behavior) and/or by external data such as certain patient health parameters and/or certain requests by the user.

The modeling of procedures in the form of a script according to the invention serves to define what tools and what drugs to use, under constant observation of linked parameters and/or signals, when and how to use these without contravening constraints etc. The rules for constraints are such that they need to be true (not false) at every given moment.

The system of the invention advantageously contains an Infusion Session Manager responsible for the execution and loading of tasks and procedures. To reach the above-described goals, said Manager preferably contains a User Interface (but it can optionally access any Graphic User Interface developed externally), a Session Controller, an Infusion Controller or Drug Delivery Controller, a DataLogger Controller possibly coupled to one or more Health Monitors and a Communication Controller. Further, the Infusion Session Manager can be in contact with an Archive Manager.

The Archive Manager stores anything on the internal state of the system and stores all important data and events, so that it is possible to restart or recover actions after a power cut, a technical failure or breakdown and/or after decoupling. Preferably, both Managers can be coupled or decoupled according to wish and are as such independently transportable units. Recovery is meant to include interruption of the actions followed by a retake exactly at the stage in the surgical procedure where one had arrived. Archiving is for instance done continuously, every second or every 5 seconds.

The Archive Manager may be built-in in the system (i.e. one and the same program may be steering both the Infusion Session Manager and the Archive Manager). Alternatively, a separate program may exist that steers the Archive Manager. This depends on the resources available to implement the system.

In the above system, a Graphical User Interface is optional in the sense that the system can be coupled to an external Display Server (X11R5) if wanted. The graphical user interface may be used to trigger or start procedures (below) after input from a minimal amount of data such as patient type and health condition, type of operation, drugs to use, tools to use etc. The Graphical User Interface further will show the values of health parameters that are measured and/or show the possible interpretation of these values. The Graphical User Interface will further show any messages, comments, warnings and/or questions on a screen, such as the question to confirm a request or to confirm continuation in a given direction. Preferably, each command given to the system via the graphical user interface has to be validated or confirmed, certainly if that command is not in the line of the expected.

Advantageously, the person in charge (anesthetist, clinician, nurse, assistant) can set via this interface the level of assistance desired, in accordance with his experience (e.g. level 1, 2 or 3).

The Communication Controller is there to guarantee efficient working of pumps and monitors throughout the surgical operation. This includes the fact that the system will not allow too fast switches in drug concentrations and/or drug types as the valves of the pumps will otherwise block and/or deregulate.

The Procedures

The anesthetic procedures according to the invention comprise a set of tasks and/or commands, in this case for instance drug delivery or the measuring of health parameters, to be performed in the course of a surgical action for a given type of patient with different steps for the different phases in a given type of surgical operation. The strict following of a procedure and/or a possible deviation therefrom depends on the status of the patient and his or her reactions to the drugs delivered and/or the surgical operation itself and/or may depend on the choice of the anesthetist in charge.

Drugs can be anesthetic drugs and/other drugs. Intravenous anesthetic drugs include among others hypnotics, analgesics and amnesics. Propofol and remifentanil are both short-acting drugs with a short half-time. The preferred hypnotic nowadays is propofol, the preferred analgesic nowadays is remifentanil, and the preferred muscular relaxing drug nowadays is mivacurium but all the other anesthetic drugs or any new anesthetic drugs that may be developed can be incorporated in the system.

The pharmacokinetic and pharmacodynamic profiles of short-acting intravenous agents, such as propofol, remifentanil, alfentanil or sufentanil, allow rapid titration of drug dose to the required effect in individual patients. Preferred drug state models are that of Schnider (Schnider et al, 1999, Anesthesiology 90: 1502-1516) for propofol and that of Minto (Minto et al, 1997, Anesthesiology 86: 24-33) for remifentanil because both models are population pharmacokinetic sets with keo values. Like fentanyl and other derivatives, remifentanil does not cause histaminoliberation not even at the highest doses. The rapid decrement of remifentanil concentrations is due to a very high plasmatic clearance (10-15 min for total degradation into inactive metabolites) by non specific esterases, the presence of which is independent of age, sex, physiopathological conditions and hepatic functions (Minto et al. 1997, Anesthesiology 86: 10-23).

Of course it is possible to use other drugs than the above proposed and/or other drug state models. In the case of pulmonary transplantation another hypnotic might be needed because propofol is apt to hepatic and pulmonary elimination (He et al, 2000, Anesthesiology 93: 986-91). A "Diprifusor" system for propofol delivery using TCI technology is on the market but the pharmacokinetic set included in the Diprifusor is that of Marsh et al. (Marsh B, White M, Morton N, Kenny G N. Pharmacokinetic model driven infusion of propofol in children. Br J Anaesth. 1991; 67 (1): 48-8) with a higher central volume than the Schnider model, that tends to overdose propofol.

Other drugs include drugs other than hypnotics, analgesics and/or amnesics that are applied in the course of a surgical operation performed under sedation or general anesthesia. Other drugs include but are not limited to paralyzing agents, vasodepressors, pressor substances and/or any type of drugs applied in cancer therapy, including antibiotics.

The preparation of tools, drug dilutions, target concentration of anesthetic and/or other drugs to generate in accordance with for instance the type of medical intervention by surgery and/or therapy and the major steps or events therein, are effectively different for a healthy patient (ASA 1 or 2) in comparison with a patient in a bad general physical condition (ASA 3, 4 or 5). ASA scores, well known in the art, are most commonly used to reflect the health condition or status of a patient. Other input or output with respect to patient information may include data on sex, age, weight, possible allergies, etc.

Each procedure is linked to the tools needed (such as drugs, pumps, syringes and other equipment, theoretical models such as pharmacodynamic, pharmacokinetic and/or posology models), to the conditions for use (such as material configuration, type of surgery, type of patient), the elementary tasks to perform (such as drug delivery and registering of vital parameters), and comments, data or measurements to archive (the logbook). A procedure is triggered or launched either by internal rules (interaction parameters) and/or by external events (the event table) or settings by the user (the user clicks, selects or enters data). The system incorporates at least the necessary minimal safety measures or constraints (the rules for safe operation) which require that in all cases and at all times the conditions for safe use must be met. For instance, certain theoretical models can not be selected for certain types of patients because they are not applicable thereto without extrapolation of data. In case of non-compliance, the system will react by warning the person in charge, by asking him to confirm his choice or instructions and/or by automatically adapting the procedure when already running. Another condition for safe use is set by the compatibility or incompatibility of interactions. If certain parameters such as for instance BIS and EMG (see infra) do not correspond or are incompatible, automatically one or more adaptations to the running procedure will be triggered. In the logbook the following are registered: all errors encountered in the course of a procedure, any inadequate handlings by the person in charge, any comments or measurements of which the registry is required further to the rules of safe use, anything on the state on any moment and anything on state transitions, any commands and changes therein, in other words the whole history of the system. For each of the tools used, such a logbook is kept to guarantee a smooth and adequate operation. The whole of the procedure is also referred to as a session.

Figure 1:
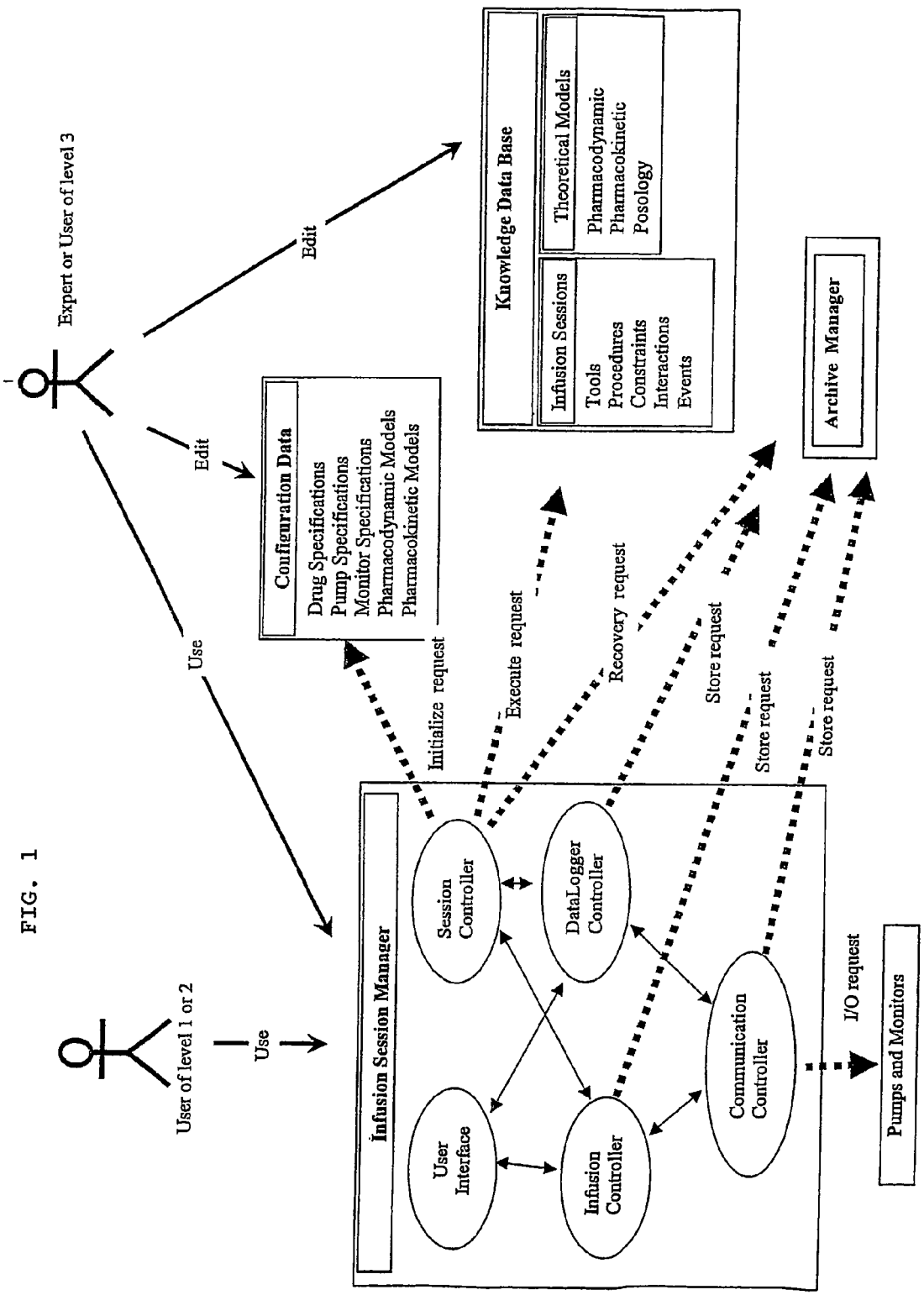
Figure 2:
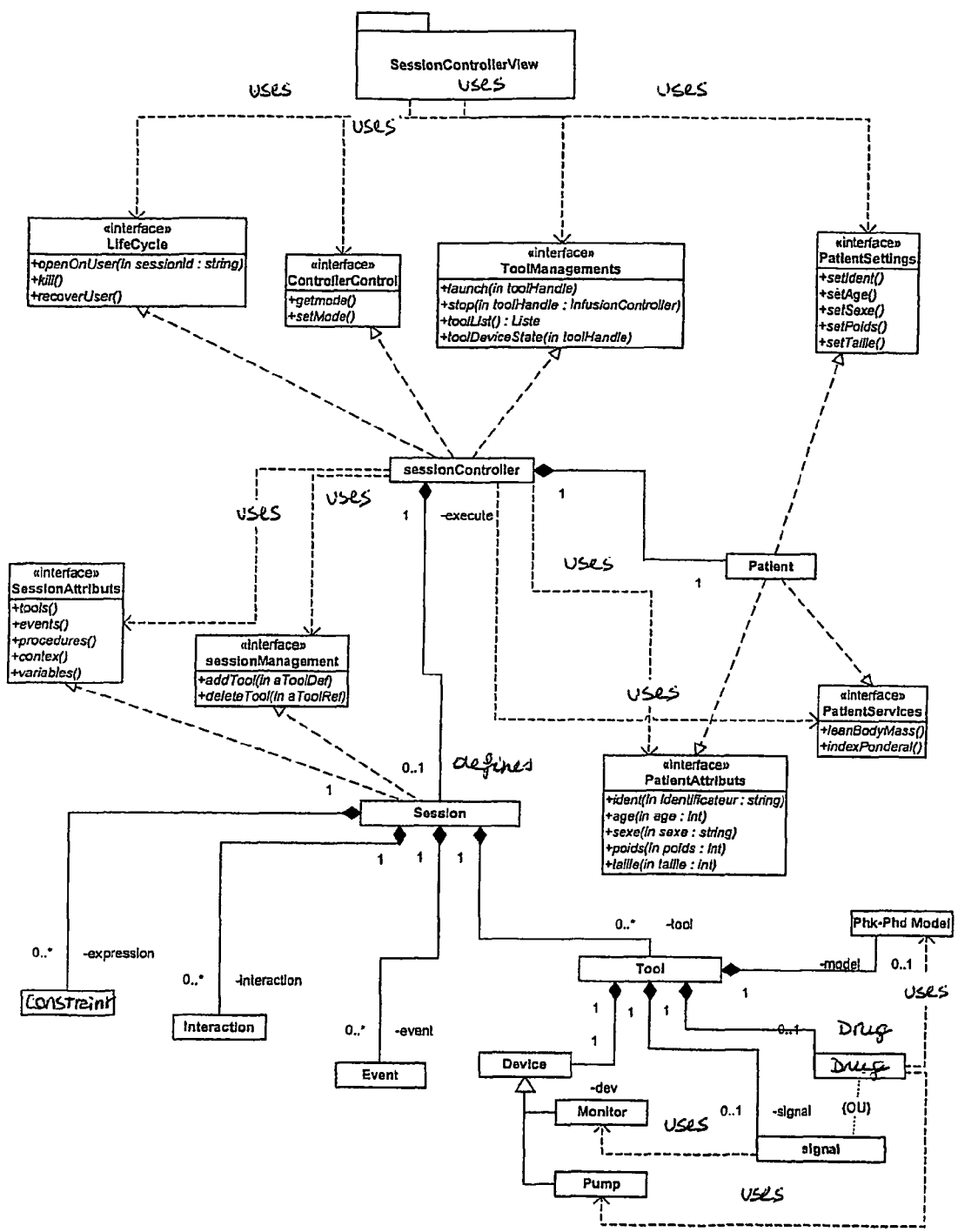

Each step of the procedure ensuring the application of a determined amount of drugs or the measuring of a given patient health parameter is effected by a session tool. For instance, for each drug an infusion pump and one or more theoretical models are made available. There are three possible ways of injection: (1) the manual type, (2) the target type (when pharmacokinetic data are available) and (3) the effect type (when also pharmacodynamic data are available). In accordance with the information available for the drug of choice, the anesthetist or assistant in charge will decide what type of injection to use. With respect to vital signals to be measured corresponding monitors and/or the necessary software for the interpretation and validation of signals (acceptability of values or not) are made available. The functioning of these tools, initially set by the selected procedure, is at all moments adjustable according to circumstances set by the person in charge and/or set by the implemented regulations for safe use. Infusion pumps can be programmed to perform certain actions automatically based on trigger combinations (parameter ranges output by a data logger). As long as the parameter(s) remain within a given range, nothing changes. Outside the range and possibly also according to the evolution of certain other parameters the system undertakes a correction action. Also, a user or person in charge can request a modification to the running procedure further to an event such as a bad, uncommon or unexpected patient response like a precocious wakening in the absence of any intervention. Whether any modifications made to the procedures by the user are or will be accepted by the system as a permanent change or not, depends on the qualification level of the user. According to an embodiment of the invention three levels of expertise are set: that of any user (level 1), that of a qualified user (level 2) and that of an expert (level 3, e.g. an anesthetist that is experienced and whose expertise may be transferred to others via the system of the invention). The Expert (or User of level 3) is the only one allowed to launch permanent changes to the system and/or to system and/or to edit the written procedures. In other words, an expert or User of level 3 is allowed to edit the Configuration data and/or the Knowledge Data Base containing the Infusion Sessions and any Theoretical Models to use (see FIG. 1) whereas a User of Level 1 or 2 is not.

Election of the Appropriate Procedure and Possible Interactivity

A procedure or script of tasks and/or commands is selected and then launched by setting or specifying initial data such as patient type and health condition, type of surgical operation, drugs, tools and models to use etc. This is further referred to as configuration of the data and initialization of the request. It is possible to have the system suggest or propose part of these data such as pharmacokinetic models and for instance monitors or appropriate pumps to use.

Further to this initialization, the most appropriate procedure is then selected from the knowledge data base and launched when the anesthetist or other person in charge gives a start command. This start command will start execution of the request or selected procedure.

The Knowledge Data Base has stored theoretical models, such as pharmacodynamic, pharmacokinetic and posology models and infusion sessions. The latter comprise procedures but also data on tools, constraints, interactions and events further to which a modulation of the procedure is recommendable and/or necessary. The system is further also capable of automatically learning from data stored in the archives of various patients with similar surgical characteristics and health condition. Upon recognition of these similarities, the system then proposes the application of one or more selected procedures or algorithms, from which the parameters can be dynamically tuned by the user.

The anesthetic procedures contain various preprogrammed commands or tasks with possibly different commands or tasks for each of the major steps, phases or events in a surgical operation. The fact is that each type of surgery is associated with a sequence of foreseeable, reproducible and stereotype steps or events for which tasks can be preprogrammed. For instance, a classical intestinal surgical operation in general starts with an induction phase of general anesthesia followed by endotracheal intubation, a preparative phase of the field of operation, surgical incision followed by a high pain stimulus during the intra-abdominal phase. Also cardiac surgical operations are characterized by a sequence of such repetitive events.

For each kind or surgical action, the succession of stimuli in general follows a dose scale parallel with similar individual responses. For instance, the stimulus associated with endotracheal intubation is generally of the same intensity as that of a skin incision. The maximal stimulus during an intestinal intra-abdominal surgical action is superior to the intensity of the stimulus associated with endotracheal intubation. For each of these steps with different pain stimulus, other drug plasmatic concentrations and flow rates and possibly a variation in drug types or drug combinations will be suggested in the procedure. For steps with the same pain stimulus the same drug plasmatic concentrations and flow rates and the same drug composition may be prescribed.

Possible predefined events of a standard surgical operation include the following: the events of sedation, induction, loss of consciousness, preintubation, haemodynamic response, the event of preparing the start of surgery, of start surgery, mean and major surgical stimulus and finally landing. Sedation requires a certain minimal concentration of hypnotics and/or analgesics that diminishes a patient's stress and decreases at the same time his awareness. Induction aims at finding the concentration of both hypnotics and analgesics that lead to unconsciousness. The session proposes effective concentrations of these agents according to the patient's physical condition. All the above-mentioned events are well known to a person skilled in the art.

In the course of the surgical operation, the anesthetist will ask the system to save or memorize certain values such as the plasmatic drug concentration at which the patient lost consciousness, values at which a haemodynamic response was observed or at the contrary was absent etc and/or he may ask to save any internal states of the Session Manager that determine future reactions and behaviors of the system. This is highly useful because some of the procedural steps may for instance be in the form of "x times the concentration at which the patient lost consciousness". These values may be archived in the logbook in case an Archiving Manager is used and serve as reference values for the rest of the course of the surgical operation.

Patient Health Parameters and Possible Changes to the Procedures in Function of Deviations During the course of the operation one or more patient health parameters are generally followed in time. The advantage of following parameters in time, continuously or for instance every 1, 2, 5, 10, 15, 20 or 30 seconds, is that useful values or numbers such as minimal and maximal values, means, coefficients of variation, a slope etc. can be obtained and/or calculated. These values are also referred to as "filtered values". Preferably a "safe" range is set for each health parameter to measure (i.e. an acceptable or tolerable minimum and maximum value are defined for said parameter(s)). For instance, a Bis value should preferably fall between 45 and 60 for a given type of patient. When a parameter falls no longer within its "safe" range set for this parameter and/or deviates from the "safe" range or a "normal" value, this is an indication that something is going wrong. This "safe" range may be set at the beginning or in the course of surgery. "Safe" ranges may also be modified by the person in charge in the course of surgery. Said "safe" ranges are used in the framework of interactions and as such may be internal triggers of a procedure.

Some patient parameters will be standard monitored, other or typical for a given kind or surgery and/or therapy. For instance, for pulmonary transplants the following parameters will be measured: continuous ECG (electrocardiogram) registration with analysis of the ST segment (myocardial ischemia detection), invasive arterial pressure, continuous registration of right pressures via a Swan-Ganz catheter in the pulmonary artery, cardiac flux, venal oxygen saturation, transoesophageal echocardiography. These are all parameters linked to haemodynamic surveillance. Respiratory control among others includes the placement of an intubation catheter with double light, the monitoring of insufflation pressures, capnography, arterial and venal oxygen saturation in blood samples. All these parameters need to be continuously surveyed by the anesthetist because a modification in these haemodynamic and respiratory parameters requires an immediate therapeutic action to prevent as much as possible brutal and detrimental events such as cardiac arrest.

Moreover, it is perfectly possible to use thoracic peridural analgesia per and post-operatively to get rapid extubation and optimal postoperative analgesia. This requires also the control of hypnotics and opioid drugs as well as the monitoring of the level of muscle paralysis to avoid systemic antagonization of muscle paralysis at the end of the surgical intervention.

A bi-spectral (Bis) analysis of an EEG may serve to survey the depth of hypnosis and unconsciousness during general anesthesia or the level of sedation (Drummond Anesthesiology 2000). The Bis index can vary from 0 to 100. A Bis index close to 100 would be representative for wakefulness whereas a low Bis index is supposed to be associated with deep levels of sedation. A Bis index incorporates phase correlation of EEG (electroencephalogram) waves as well as EMG (electromyography) and the percentage of electric silence in the signal.

As the BIs index is often blown up, it is advantageous to measure a patient's EMG at the same time to be able to identify such blown up Bis index numbers. It is in general advisable to measure associated signals and their interactions.

In an embodiment of the invention, the Bis index is measured every 15 seconds and with each measurement it is verified whether the Bis index still falls within a given "safe" range, for instance 45<Bis<60.

The patient's Bis index is preferably correlated with the effect-site target concentration of the hypnotic(s). Also the patient's TOF values (interpretation of the level of muscular paralysis, measured by the muscular contraction of the adductor pollicis muscle in response to an ulnar stimulus from the patient) may be measured in function of a given flux of curare and/or the patient's MAP (mean arterial pressure). As such interactions between parameters and signals can be measured, which help to set adequate values for sedation and relaxation and/or to verify that preset values in a procedure correspond with a real life situation.

As overdosing of a hypnotic can lead to hypotension, it is recommended to check for instance that the variation in MAP is low before increasing the concentration of an hypnotic.

Table 2 summarizes a patient's situation in function of its MAP and Bis and gives an example of which actions have to be taken in different clinical situations. Adaptation of hypnotic and/or analgesic levels and/or administration or correction of other drugs such as vasodilators, vasopressors are hereby in accordance with the situation represented by both recent Bis and MAP values. So, the system takes the actions an anesthesiologist would otherwise decide to take when seeing those Bis values on the monitor screen.

TABLE 2

|  | High MAP (>120% of the reference value) or tachycardia | Normal MAP | Low MAP (<80% of the reference value) or bradycardia |
| --- | --- | --- | --- |
| Bis >60 for more than 1 min | ↑ hypnotic and/or analgesic | ↑ hypnotic | volumetric expansion and/or vasopressor substances ↑ hypnotic |
| 45 < Bis < 60 | ↑ hypnotic and/or analgesic | ideal situation | volumetric expansion and/or vasopressor substances |
| Bis <45 for more than 1 min | Analgesic and/or vasodilator | ↑ hypnotic | ↑ hypnotic and/or volumetric expansion and/or vasopressor substances |

Changes in plasmatic concentration or at the level of the effect-site of the hypnotic(s) used can be achieved in various ways. For instance, they can be changed via a level fixed in advance (for instance plus or minus 10, 20, 30, 40, 50, 60, 70, 80 or 90% of an actual concentration irrespective of the Bis index) or by adapting the correction to the delta-bis value (difference between the actual and the expected Bis index) In this case it suffices to increase or diminish the hypnotic proportionally. For instance, a delta-bis of +5 will provoke an increase of 5% of the plasmatic concentration, and a delta-bis of −20 will provoke a decrease by 20%.

Preferably, the system also registers for instance, at the command of the person in charge, minimal and/or maximal limit values of physiological parameters recorded by the patient health monitor when reaching and/or exceeding a limit concentration of anesthetics and/or other drugs (see above).

Constraints and Safety Measures

The system according to the invention includes a minimal set of constraints or safety measures. These help to avoid undesired automatic actions. This concept is also referred to as the safety and/or control concept. An example of a safety measure is that the system will not allow the drop of an analgesic below a minimal concentration during the course of the operation. For instance, the brutal recovery of a patient is always possible when the propofol target is below 1.5. Another example is that it is impossible to accidentally activate a button or command that would stop the infusion of one of the drugs used before the end of the surgery.

There are 3 types of constraints foreseen in the system of the invention: time constraints, calculation constraints and constraints of appropriate functioning. The first include the calculation time, the reaction time (i.e. the time needed for a device to react to the command given, to change its current state and/or to stop its current actions) and the period of acquisition (i.e. the minimal period for a monitor to register something). Calculation constraints guarantee that every second the necessary measurements are effected, and guarantees that calculated flow rates correspond to actual flow rates of a pump before any (further) changes to said flow rate are permitted. The constraints of appropriate functioning assure that the system memorizes any requests received via the User Interface. If it is not possible to prosecute or implement the command and/or request immediately, the user is informed hereof (via the User Interface) that there is a conflict, a waiting list of commands is then generated and the situation is reconsidered every second until launch is possible (i.e. until the request can be implemented and/or fully complied with).

The procedures of the system are thus written as such that for instance a minimal amount of time will need to pass between two subsequent automatic modifications of a drug concentration. This delay may be fixed in advance and/or can be set manually. As explained above, delays are imposed by the time necessary to command for instance a pump and by the time needed to calculate the actual infusion of a drug realized following a modification to the system. Preferably no change to the system is allowed before the calculated flow rate or the flow rate set corresponds to the actual flow rate of a pump. For instance, at least 10 seconds are preferably allowed at the level of pump control as the valves would otherwise deregulate and/or block. This delay is fixed and can not be modified by the person in charge. The delay needed for adequate pump control may vary from about 10 to about 30 seconds.

Another safety measure that can be included is the comparison of actually measured values with for instance median values, mean values (for instance the mean value over the preceding minute), moving averages or moving medians registered by the patient health monitor over a given period of time or any other calculated parameter of interest. These values are also referred to as "filtered" values.

Preferably a "normal" value and/or a "safe" range is defined for each of the parameters. Drug concentrations may then be automatically adapted whenever they depart from said normal value and/or are no longer contained within the given "safe" range. For instance, the actual concentration of anesthetics and/or other drugs may be automatically changed whenever the BIs index is lower than 45 or higher than 60 and/or whenever the MAP departs from its normal value (see Table 2). By comparing actual and mean values one may also avoid undesired automatic actions. In case of too large a deviation, an interaction and/or correction by the user or person in charge may be desirable.

Another safety measure may exist in the automatic and rapid decrease of the propofol target concentration or flow rate according to the BIS values as such that the propofol concentration will not drop below a predetermined value of for example 1.5 µg/ml.

Still another safety measure may exist in the warning of the person in charge by way of a signal such as a sound or by way of a written message in case of an inappropriate handling or instruction or in case certain health parameters deviate unexpectedly. Any automatic adaptation of a parameter could be advertised by an alarm signal.

In order to safeguard a reliable measurement of health parameters such as the Bis index, also the quality of said signal and/or the value of other related signals can be taken into consideration. For instance, if the Bis value is not corresponding to a given EMG value, this Bis value is considered unreliable. Whenever the quality of the measured signal drops below a predefined threshold, the system will provoke the following actions: (i) warn the user and (ii) leave the automated closed-loop and revert to manual mode. This is done following the observation that a constraint is false (and not true). A check will be performed on a regular basis, for instance each second, each 5 seconds, each 10 to 30 seconds, each minute or every 5 minutes.

In other words, the reliability of a signal or parameter may be determined or defined by the quality of its signal, by its relation with other related signals or parameters and/or by the deviation from a normal value and/or from a safe range.

Still another safety measure may exist in the warning in case a drug concentration is set (by the person in charge) outside the normal range used for that drug.

The system of the invention has hitherto been mainly explained for applications in intravenous anesthesia. The system is, however, equally well applicable to other medical fields such as for instance cancer therapy wherein drugs and possible also antibiotics may be intravenously administered.

The invention will be described in further details in the following examples, by reference to the enclosed drawings. Embodiments (see above) and examples (see below) are not in any way intended to limit the scope of the invention as claimed.

EXAMPLES

Example 1

A Healthy Patient Subjected to a Standard Type of Surgery

The following procedural steps give an example for a patient in good health (ASA2) that will undergo a standard surgical operation.

Event sedation=0.5 µg/ml propofol

Event induction=1.5 µg/ml propofol +2 ng/ml remifentanil. The hypnotic dose is then automatically increased in subsequent steps of +0.5 to 1 µg/ml of propofol with a fixed level of analgesic (e.g. 2 ng/ml remifentanil) until the next event=loss of consciousness Event loss of consciousness=maintaining the propofol concentration at the level whereby loss of consciousness was registered. The concentration whereby loss of consciousness is obtained will be memorized on the demand of the person in charge.

Event preintubation=increasing the concentration of remifentanil up to a level suited with respect to the patient's age, physical condition, the adjuvants being administered and registered by the procedure, e.g. increase up to 4 ng/ml for a patient that is sensitive. The actually needed value is again memorized and will have consequences for the rest of the procedure, for instance in case of a haemodynamic response or in case one needs more than 4 ng/ml of remifentanil Event haemodynamic response=+2 ng/ml remifentanil Event preparing start surgery=returning to the level of hypnotic that induced loss of consciousness, with or without a level of analgesic Event start surgery=returning to the concentration of hypnotic(s) and analgesic(s) registered for an intubation when no haemodynamic response was invoked by intubation or going back to the intubation level+the increase in case of a haemodynamic response Mean surgical stimulus=incision level*1.5

Major surgical stimulus=incision level*2

An important haemodynamic response brings about a greater sensibility of titration with regard to the analgesic Landing=synchronized return to the level of hypnotic that invoked unconsciousness at the effect-site together with an analgesic level associated with a lack of major respiratory depression Example 2

An Unhealthy Patient Subjected to Cardiac Surgery

The following procedural steps give an example for a patient in poor health (ASA4) that will undergo an aortic valve replacement.

Event sedation=0.25 µg/ml propofol

Event induction=1 µg/ml propofol+1.5 ng/ml remifentanil. The hypnotic dose is then automatically increased in subsequent steps of +0.25 µg/ml of propofol with a fixed level of analgesic (e.g. 1.5 ng/ml remifentanil) until the next event=loss of consciousness Event loss of consciousness=maintaining the propofol concentration at the level whereby loss of consciousness was registered. The concentration whereby loss of consciousness is obtained will be memorized on the demand of the person in charge. This event will be associated with the start of the infusion sequence of the muscle relaxant used if there is one.

Event preintubation=increasing the concentration of remifentanil up to 3 ng/ml. The actually needed value is again memorized and will have consequences for the rest of the procedure, for instance in case of a haemodynamic response or in case one needs more than 3 ng/ml of remifentanil Event haemodynamic response=+1 ng/ml remifentanil Event preparing start surgery=returning to the level of hypnotic that induced loss of consciousness, with or without a level of analgesic. Start of closed loop propofol administration between the effect-site concentration of propofol and the BIS level. Each time the BIS will go over or below the predefined BIS range limits, the automatic adaptation of the propofol site effect will be done.

Event start surgery=returning to the concentration of hypnotic(s) and analgesic(s) registered for an intubation when no haemodynamic response was invoked by intubation or going back to the intubation level+the increase in case of a haemodynamic response Mean surgical stimulus=remifentanil incision level*1.25

Major surgical stimulus=remifentanil incision level during a mean surgical stimulus*1.5

Landing=synchronized return to the level of hypnotic that invoked unconsciousness at the effect-site together with an analgesic level associated with a lack of major respiratory depression

The invention claimed is:

1. A computer-aided intravenous drug delivery system delivering a drug to a patient during a whole duration of an anesthetic procedure during which an anesthetic is delivered to the patient, the system comprising:

an editable knowledge base that stores a set of written procedures and theoretical procedure models to steer intravenous delivery of drugs for the anesthetic procedure, the written procedures adapted to types of surgical actions, physical conditions of patients, types of drugs, tools used to administer the drugs, and theoretical models of the drugs, the set of written procedures including at least a first procedure and a second procedure;

a sensor coupled to the patient, the sensor generating a signal that reflects a health condition or status of the patient;

an Infusion Session Manager delivering the drug for the anesthetic procedure, the Infusion Session Manager comprising:

an Infusion Controller arranged to deliver an amount of the drug intravenously to the patient for the anesthetic procedure;

a Communication Controller connected with infusion pumps and monitors;

a DataLogger controller that receives the signal from the sensor;

a Graphical User Interface comprising displays of different views of the system and that accepts user input;

a first interface forming a link between the Infusion Controller and one of the views displayed by the Graphical User Interface;

a dynamically adaptive Session Controller that runs the first procedure, the dynamically adaptive Session Controller dynamically adapting the first procedure in real time during the anesthetic procedure based on the signal from the sensor or an observation from a user of the drug delivery system, or the dynamically adaptive Session Controller selecting and running the second procedure based upon the signal from the sensor or the observation from the user;

a second interface forming a link between the dynamically adaptive Session Controller and the views displayed by the Graphical User Interface; and a third interface forming a link between the DataLogger Controller and the views displayed by the Graphical User Interface;

a plurality of settings for different experience levels of the user controlling the ability of the user to make changes to the system;

wherein the plurality of settings includes a setting for an expert experience level and wherein permanent changes to the knowledge database and written procedures may be made only if the user has an expert level of experience.

2. The system according to claim 1, further comprising:
an Archiving Manager which is in contact with the Infusion Session Manager, the Archiving Manager storing data needed to restart or recover actions after a power cut, a technical failure, breakdown, or decoupling; and
a program that controls the Infusion Session Manager and the Archiving Manager.

3. The system according to claim 2, wherein the Archiving Manager and the Infusion Session Manager are independently transportable units.

4. The system according to claim 1, wherein a running procedure in the set of written procedures is launched or changed in response to an internal state or in response to an externally received command.

5. The system according to claim 1, wherein at least one of the written procedures contains a preprogrammed script of tasks or commands per major event, phase or step in a surgery.

6. The system according to claim 1, wherein the Infusion Controller administers at least one intravenous drug selected from a group consisting of a hypnotic, an analgesic, an amnesic, a paralyzing agent, a vasodepressor and a pressor substance and a cancer therapy drug.

7. The system according to claim 6, wherein the hypnotic is propofol.

8. The system according to claim 7, wherein a drug state model for propofol is that of Schnider.

9. The system according to claim 6, wherein the Infusion Controller administers the cancer therapy drug in combination with antibiotics.

10. The system according to claim 6, wherein the analgesic is remifentanil.

11. The system according to claim 6, wherein the paralyzing agent is mivacurium.

12. The system of claim 10, wherein a drug state model for remifentanil is that of Minto.

13. The system according to claim 1, wherein the system is adapted to perform a delay requiring a minimal amount of time has to pass between two subsequent modifications to one of the written procedures.

14. The system according to claim 1, wherein a reliability of the signal is determined by a quality of the signal, by a relation of the signal with other related signals or parameters, or by a deviation of the signal from a normal value or from a safe range.

15. The system of claim 1, wherein the Graphical User Interface shows the signal generated by the sensor, measured values of health parameters, or interpretations of the measured values of the values of the health parameters.

16. The system of claim 1, wherein the signal generated by the sensor reflects values of health parameters selected from a group consisting of: continuous ECG, registration with analysis of a ST segment, invasive arterial pressure, continuous registration of right pressures via a Swan-Ganz catheter in a pulmonary artery, cardiac flux, venal oxygen saturation, tranesophageal echocardiography, monitoring of insufflations pressures, capnography, arterial and venal oxygen saturation in blood sample or a mixture thereof.

17. The system of claim 1, further comprising a patient health monitor of minimum or maximal limit values of physiological parameters recorded when reaching or exceeding a limit concentration of the drug, the patient health monitor being connected to the DataLogger controller.

18. The system of claim 1, wherein the set of written procedures is in the form of a script.

19. A method for intravenous anesthesia by a computer-aided intravenous delivery system of a drug to a patient during a whole duration of an anesthetic procedure in which an anesthetic is delivered to the patient, the system comprising:
an editable knowledge base that stores a set of written procedures to steer intravenous delivery of drugs for the anesthetic procedure, the written procedures adapted to types of surgical actions, physical conditions of patients, types of drugs, tools used to administer the drugs, and theoretical models of the drugs, the set of written procedures including at least a first procedure and a second procedure;
a sensor coupled to the patient;
an Infusion Session Manager controlling delivery of the drug for the anesthetic procedure, the Infusion Session Manager comprising:
an Infusion Controller arranged to deliver an amount of the drug intravenously to the patient for the anesthetic procedure;
a Communication Controller connected with infusion pumps and monitors;
a DataLogger controller that receives the signal from the sensor;
a Graphical User Interface displaying a plurality of views of the system and that accepts user input;
a first interface linking the Infusion Controller to one of the views displayed by the Graphical User Interface;
a Session Controller configured to control the first procedure,
a second interface linking the Session Controller to the views displayed by the Graphical User Interface; and
a third interface that links the DataLogger Controller to the views displayed by the Graphical User Interface;
a plurality of settings for different experience levels of a user of the system controlling the ability of the user to make changes to the system, wherein the plurality of settings includes a setting for an expert experience level and wherein permanent changes to the knowledge database and written procedures may be made only if the user has an expert level of experience;
the method comprising:
the sensor generating a signal that reflects a health condition or status of the patient;
the DataLogger controller of the Infusion Session Manager receiving the signal from the sensor;
displaying at least one of the views on the Graphical User Interface to a user;
if the user has an expert experience level, selectively editing the knowledge database and written procedure;
the Session Controller dynamically adapting the first procedure in real time during the anesthetic procedure based on the signal from the sensor to the Datalogger controller of the Infusion Session Manager or an observation from the user and delivering a controlled amount of the drug intravenously to the patient, or
the Session Controller selecting and running the second procedure based upon the signal from the sensor from the sensor to the Datalogger controller of the Infusion Session Manager or the observation from the user and delivering a controlled amount of the drug intravenously to the patient.

* * * * *